United States Patent
Jaggi et al.

(10) Patent No.: US 9,051,603 B2
(45) Date of Patent: Jun. 9, 2015

(54) METHOD FOR OPTIMIZED ISOLATION OF RNA FROM FIXED TISSUE

(75) Inventors: Rolf Jaggi, Bremgarten (CH); Robert Häner, Uettligen (CH)

(73) Assignee: Universität Bern, Bern (CH)

( * ) Notice: Subject to any disclaimer, the term of this patent is extended or adjusted under 35 U.S.C. 154(b) by 1242 days.

(21) Appl. No.: 12/937,863

(22) PCT Filed: Apr. 8, 2009

(86) PCT No.: PCT/EP2009/002596
§ 371 (c)(1),
(2), (4) Date: Jan. 3, 2011

(87) PCT Pub. No.: WO2009/127350
PCT Pub. Date: Oct. 22, 2009

(65) Prior Publication Data
US 2011/0111967 A1 May 12, 2011

(30) Foreign Application Priority Data

Apr. 15, 2008 (EP) .................................... 08007347

(51) Int. Cl.
*C12Q 1/68* (2006.01)
*C12N 15/10* (2006.01)
*C07H 21/00* (2006.01)

(52) U.S. Cl.
CPC .......... *C12Q 1/6806* (2013.01); *C12N 15/1003* (2013.01)

(58) Field of Classification Search
CPC .. C12N 15/10; C12N 15/10003; C12N 15/11; C12N 15/1003; C12Q 1/6806
See application file for complete search history.

(56) References Cited

U.S. PATENT DOCUMENTS

| 5,346,994 A | * | 9/1994 | Chomczynski ................ 530/419 |
| 6,248,535 B1 | * | 6/2001 | Danenberg et al. .......... 435/6.12 |
| 2007/0026432 A1 | * | 2/2007 | Ke et al. ............................. 435/6 |

FOREIGN PATENT DOCUMENTS

| EP | 1743939 A2 | 1/2007 |
| WO | 01/46402 A1 | 6/2001 |

OTHER PUBLICATIONS

Pabon et al. (Biotechniques, 2001, 31(4):874-879).*
Stangegaard et al. (Biotechniques, 2006, 40:649-657).*
Oberli, Andrea et al., "Expression Profiling With RNA From Formalin-Fixed, Paraffin-Embedded Material" BMC Medical Genomics, Apr. 19, 2008, vol. 1, No. 9, BioMed Central Ltd.
International Search Report for PCT/EP2009/002596 dated Jul. 28, 2009 (4 pages).

* cited by examiner

*Primary Examiner* — Christopher M Babic
*Assistant Examiner* — Jeremy C Flinders
(74) *Attorney, Agent, or Firm* — McCormick, Paulding & Huber LLP

(57) ABSTRACT

In invention relates to a method for the isolation of RNA from tissue pretreated with formaldehyde comprising homogenizing the sample in the presence of a guanidinium salt in aqueous solution, and incubating the sample in the presence of 0.1 M to 5 M ammonium salt at a temperature between 50° C. and 100° C. The heat treatment in the presence of an ammonium salts demodifies RNA by reverting methylol groups which are formed in the presence of formaldehyde between amino groups in nucleobases of RNA and in basic amino acids, and by cleavage of methylene bridges between amino groups in nucleobases of RNA and basic amino acids, to provide high RNA recoveries and consistently high quality of RNA for further reaction, e.g. for reverse transcriptase-polymerase chain reaction or microarray analysis.

15 Claims, 6 Drawing Sheets

SEQUENCE LISTING

```
<160> NUMBER OF SEQ ID NOS: 6

<210> SEQ ID NO 1
<211> LENGTH: 39
<212> TYPE: DNA
<213> ORGANISM: artificial
<220> FEATURE:
<223> OTHER INFORMATION: synthetic construct, T7 primer carrying
      randomized nucleotides at the 3' end
<220> FEATURE:
<221> NAME/KEY: misc_feature
<222> LOCATION: (30)..(39)
<223> OTHER INFORMATION: n is a, c, g, or t

<400> SEQUENCE: 1
gaatggtaat acgactcact atagggagan nnnnnnnnn                              39

<210> SEQ ID NO 2
```

-continued

```
<211> LENGTH: 19
<212> TYPE: DNA
<213> ORGANISM: artificial
<220> FEATURE:
<223> OTHER INFORMATION: synthetic construct, GAPDH forward primer

<400> SEQUENCE: 2
cagccgcatc ttcttttgc                                                    19

<210> SEQ ID NO 3
<211> LENGTH: 20
<212> TYPE: DNA
<213> ORGANISM: artificial
<220> FEATURE:
<223> OTHER INFORMATION: synthetic construct, GAPDH reverse primer
      (short)

<400> SEQUENCE: 3
ccatggtgtc tgagcgatgt                                                   20

<210> SEQ ID NO 4
<211> LENGTH: 13
<212> TYPE: DNA
<213> ORGANISM: artificial
<220> FEATURE:
<223> OTHER INFORMATION: synthetic construct, GAPDH probe

<400> SEQUENCE: 4
tcgccagccg agc                                                          13

<210> SEQ ID NO 5
<211> LENGTH: 17
<212> TYPE: DNA
<213> ORGANISM: artificial
<220> FEATURE:
<223> OTHER INFORMATION: synthetic construct, GAPDH reverse primer
      (medium-length)

<400> SEQUENCE: 5
accaggcgcc caatacg                                                      17

<210> SEQ ID NO 6
<211> LENGTH: 28
<212> TYPE: DNA
<213> ORGANISM: artificial
<220> FEATURE:
<223> OTHER INFORMATION: synthetic construct, GAPDH reverse primer
      (long)

<400> SEQUENCE: 6
gcaacaatat ccactttacc agagttaa                                          28
```

METHOD FOR OPTIMIZED ISOLATION OF RNA FROM FIXED TISSUE

CROSS REFERENCE TO RELATED APPLICATIONS

This application claims the benefit of PCT Application No. PCT/EP2009/002596, filed on Apr. 8, 2009 and European Patent Application No. 08007347.1, filed Apr. 15, 2008, the disclosures of which are herein incorporated by reference in their entirety.

FIELD OF THE INVENTION

The present invention relates to the field of molecular biology and provides a novel method and reagent for the isolation and demodification of ribonucleic acid (RNA) from formalin-fixed, paraffin-embedded tissue.

This application includes and incorporates by reference a Sequence Listing which is attached hereto as an Appendix. The Sequence Listing contains six sequences identified by numbers 1-6.

BACKGROUND OF THE INVENTION

RNA from formalin fixed and paraffin embedded material is chemically modified and cross-linked with other nucleic acids and with proteins preventing efficient isolation, and many fundamental experiments in the field of molecular biology are inhibited or very inefficient. Before RNA can be used efficiently for quantitative and qualitative analyses, e.g. reverse transcription followed by PCR, quantitative PCR and synthesis of probes for DNA microarrays, these modifications must be removed. Such a process is called demodification.

Several published reports describe methods to isolate RNA from fresh (or quick frozen) and from formalin fixed, paraffin embedded (FFPE) cells or tissues. Most of these techniques utilize a cell or tissue disruption step in which the tissue is dispersed in a powerful protein denaturation solution containing a chaotropic agent (e.g. guanidinium or lithium salt). This rapid disruption of cell membranes and inactivation of endogenous ribonuclease is critical to prevent degradation of RNA during purification and isolation.

Generally, RNA is used to gain information on the expression of genes in tissue samples. Methods are often based on quantitative reverse transcription-polymerase chain reaction (qRT-PCR), probably the most sensitive and reliable assay available for quantification of RNA. The qRT-PCR method tolerates fragmentation of starting RNA to some degree and protocols are available to make the measurement robust and reproducible. Another important technological application is microarray expression profiling which is another method based on RNA which also involves a reverse transcription step. It is distinct from qRT-PCR as so far it depends on high quality RNA and special methods are required which tolerate fragmentation of RNA.

RNA is a particularly labile molecule, it is susceptible to nonspecific degradation by physical conditions, mainly heat, high or low pH, or biochemical degradation by endogenous and exogenous RNAses. Intactness of RNA is crucial for a number of applications like polymerase-mediated linear amplification, Northern analysis, RNase protection assays and microarray analysis with standard methods.

Treatment of RNA with aldehyde fixatives such as formaldehyde (paraformaldehyde, formalin) causes chemical modification (addition of methylol groups to amino groups) in RNA, DNA and proteins and intra- and intermolecular crosslinking of RNA strands and crosslinking of RNA with protein through methylene bridges. Treatment of tissue with fixatives like formaldeyde or paraformaldehyde compromises the isolation of RNA from tissue using standard protocols like chaotropic agents or phenol-based methods. Efficient extraction can only be achieved when proteolytic enzymes like proteinase K or other proteases are used to digest crosslinked proteins into small peptides. Nucleic acids become soluble, although small peptides may remain attached (cross-linked). Proteolytic digestion with protease does not usually destroy crosslinks and chemical modifications in RNA, and methylol groups which are bound to amino groups of nucleobases remain preserved. Some procedures have been described to partially revert these modifications, but a major challenge remains that demodification and recovery of RNA from archival material are highly variable, and down-stream applications are sensitive towards varying amounts of residual modifications.

Usually, partial fragmentation of RNA by the action of endogenous RNases is not an important issue because the material is normally processed for histological analyses, which are not affected by this process and therefore, no special precautions are taken to reduce or prevent RNA degradation. In many situations, the starting material is an archival sample, which has been prepared earlier in the context of routine diagnosis or in the context of clinical trials. RNA prepared from routinely processed tissue is in the range of several hundred nucleotides, and only a small fraction of RNA comprises less than 100 nucleotides. Degradation of RNA to this size does not greatly affect methods like qRT-PCR, and therefore, RNA from archival material might be a perfect substrate for gene expression measurement when carried out with gene-specific primers during reverse transcription, and when PCR is performed with primers coding for amplicons which are smaller than hundred base pairs.

The use of high recoveries of RNA is fundamental for performing various molecular biological assays and experiments, such as normal RT-PCR, qRT-PCR and microarray experiments. The intrinsic instability of RNA and the presence of endogenous RNases in tissues makes the isolation of intact RNA a difficult procedure, but partially degraded RNA can be isolated. Although the contamination of molecular biology laboratories with RNases is usually not the major source of low quality RNA in this context, there is an ongoing need to develop improved techniques, which make RNA isolation and detection assay methods more sensitive, more specific, faster, and less susceptible to partial degradation. Ideally, it would be advantageous for research facilities in many instances to use an automated RNA isolation protocol, in order to combine it with rapid RNA assay techniques or integrated nucleic acid diagnostic devices for efficient, automated RNA isolation and analysis.

All the current protocols are based on reagents and protocols to minimize RNA degradation by endogenous and exogenous RNases, but they do not usually use reagents to eliminate chemical cross-links and modifications in fixed RNA.

For example, Danenberg et al. (US 2006/0199197) present a protocol which provides an RNA suitable for reverse transcription and PCR. The protocol involves a guanidinium-containing buffer and heating to 70-90° C. Schlumpberger et al. (WO2007/068764) describe RNA isolation with a nucleophilic reagent and a heat treatment step, which should improve recovery of RNA and accessibility of the RNA for reverse transcription followed by PCR.

In view of the above, there is a need for methods and reagents that allow one to recover at high efficiency RNA (including partially degraded RNA) from tissue samples treated with formalin and embedded in paraffin followed by storage at ambient or near ambient temperature for extended periods of time.

SUMMARY OF THE INVENTION

The invention relates to a method for the isolation of RNA from tissue pretreated with formaldehyde comprising the steps of
(a) homogenizing the sample in the presence of a guanidinium salt in aqueous solution, and
(b) incubating the sample in the presence of 0.1 M to 5 M ammonium salt at a temperature between 50° C. and 100° C.

The method is particularly suited for formalin fixed, paraffin embedded tissue, such as archival biopsy material collected and stored over many years.

The guanidinium salt in step (a) is preferably guanidinium isothiocyanate, and the solution of step (a) may further comprise a detergent and/or buffer of pH 4 to 8, and optionally a proteinase such as proteinase K to destroy proteins and particularly RNases.

The ammonium salt of step (b) is preferably ammonium chloride, and may be added to the solution of step (a) as an approx. 5 M stock solution or in solid form.

Preferred incubation time in step (b) is between 1 and 300 minutes, depending on the incubation temperature.

The RNA solution obtained in the method of the invention may be purified from cell debris and reagents on a silica gel column, and the RNA obtained further processed with reverse transcriptase-polymerase chain reaction or microarray analysis.

A breast cancer specimen fixed in formalin and embedded in paraffin was homogenized in lysis buffer and digested with proteinase K. 5 M ammonium chloride solution is added and demodification continued at 94° C. for 0, 30, 60, 120 or 300 min according to Example 1. The RNA was purified from lysates on a silica-based column and analyzed on an Agilent 2100 Bioanalyzer (left panel. Outermost left lane: molecular weight ladder). Each RNA was tested by qRT-PCR for the expression of GAPDH (glyceraldehyde-3-phosphate dehydrogenase, accession number NM_002046.3) using primers coding for short (amplicon size 54 bp, -Δ-), medium-length (83 bp, -□-) and long amplicons (103 bp, -◇-) and resulting threshold cycle values (Ct) are shown for each amplicon.

Figure 2:
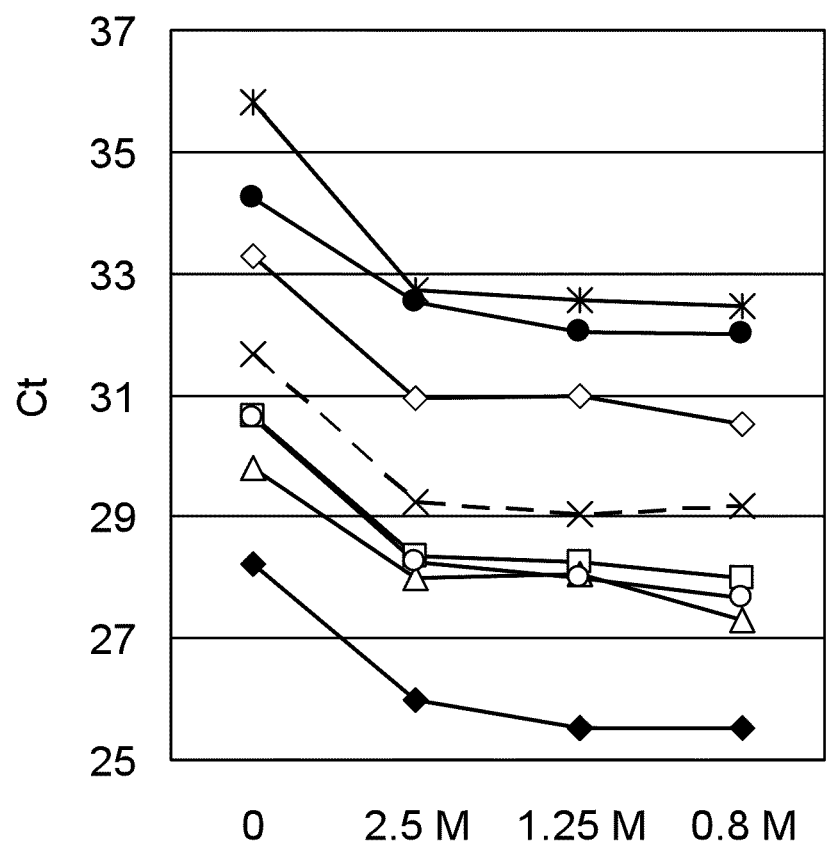

FIG. 2—Different concentrations of ammonium chloride are effective when added to proteinase K digested RNA in chaotropic lysis buffer Tissue sections were homogenized in lysis buffer according to Example 1 and untreated RNA (0) was compared to RNA that was demodified at 94° C. after addition of NH$_4$Cl to the final concentrations of 2.5 M, 1.25 M or 0.8 M as indicated. Each line represents raw Ct values for following gene-specific qPCR assays (from top to bottom): -*-IGBP5 long (Insulin growth factor binding protein 5, NM_000599.2, amplicon size 147 bp), -●-PGR (progesterone receptor, NM_000926), -◇-TFRC (transferrin receptor, NM_006461.3), --x--IGBP5 medium (amplicon size 109 bp), -□-HER2 (v-erb-b2 erythroblastic leukemia viral oncogene homolog 2, NM_001005862.1), -○-RPLP0 (ribosomal protein, large, NM_053275.3), -Δ-IGBP5 short (amplicon size 60 bp), -♦-ESR1 (estrogen receptor 1, NM_000125.2).

Figure 3:
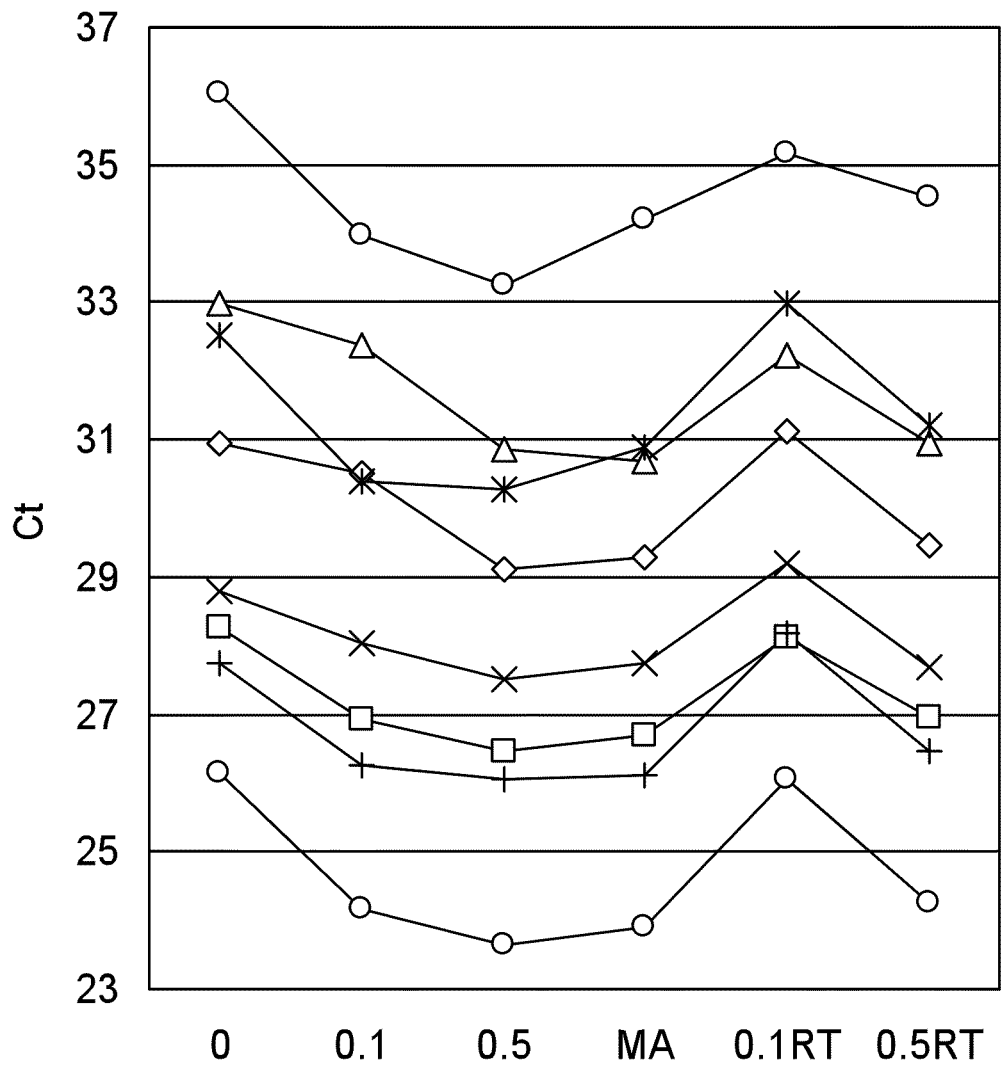

FIG. 3—Comparison of different formulations of demodification reagents

The isolated RNA was not demodified (0) or demodification was performed with 0.1 M or 0.5 M ammonium chloride by incubating at 94° C. for 20 minutes or with 6 M methyl amine (MA), 0.1 M (0.1 RT) or 0.5 M (0.5 RT) ammonium chloride at room temperature over night. Purified RNA was processed by qRT-PCR with optimized primers specific for the following genes (from top to bottom): -○-IGBP5 long, -Δ-PGR, -*-IGBP5 medium, -◇-TFRC, -x-IGBP5 short, -□-RPLP0, -+-HER2, -○-ESR1. For details see legend to FIG. 2.

Figure 4:
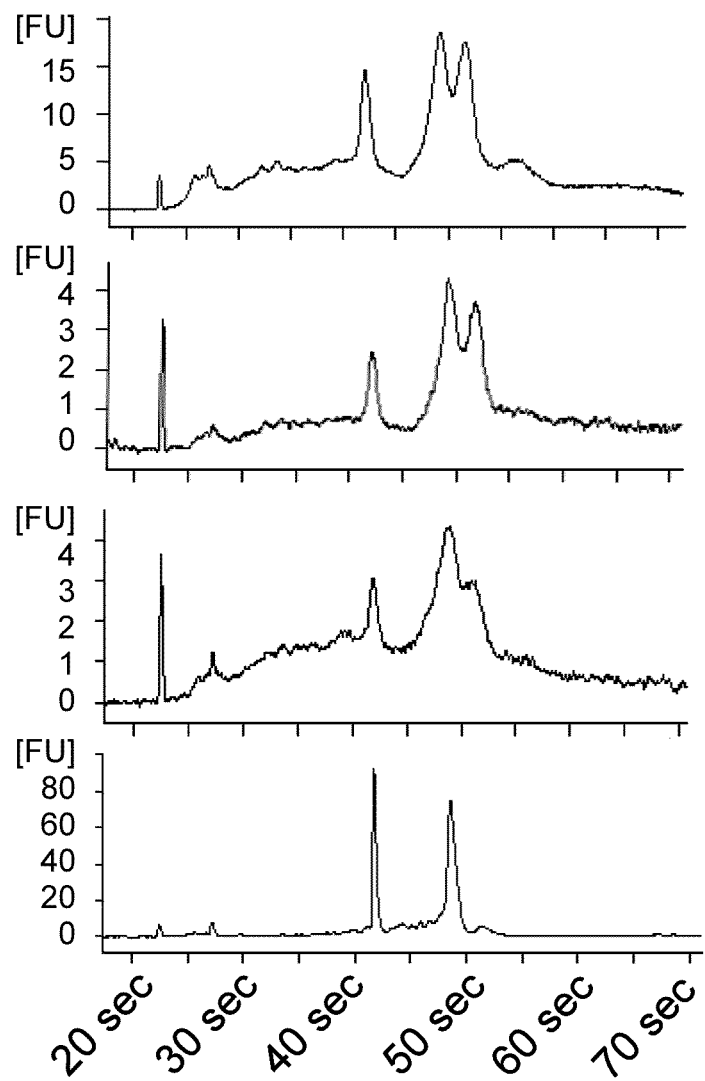

FIG. 4—Demodification reverts cross-links in formalin-fixed ribosomal RNA

Purified, intact RNA from snap frozen cells was incubated with 10% formalin at 4° C. for 16 h which leads to the formation of an additional RNA species which is apparent as additional peak after separation on an Agilent 2100 Bioanalyzer (top panel). The RNA is separated in an electric field and the RNA is measured as fluorescence [FU] relative to the separation time in seconds (sec). Small RNA species run faster than large RNA molecules. The position of the peak between 50 and 55 seconds (sec) suggests that this RNA is larger than 18 S (41 to 43 sec) and 28 S (48 to 50 sec) and most likely represents cross-linked aggregates formed between distinct ribosomal RNA molecules (e.g. between 18 S and 28 S RNA molecules). Demodification of this RNA in lysis buffer after incubation with 5 M ammonium chloride for 3 min (second panel from top) or 20 min (third panel from top) at 72° C. leads to a partial disappearance of this additional RNA peak. The sizes of the 18 S and 28 S peaks are not or only to a small proportion affected by this treatment suggesting that the disappearance of the additional peak is not a result of nonspecific degradation of RNA during demodification. Intact, untreated RNA is shown in the lowest panel.

Figure 5:
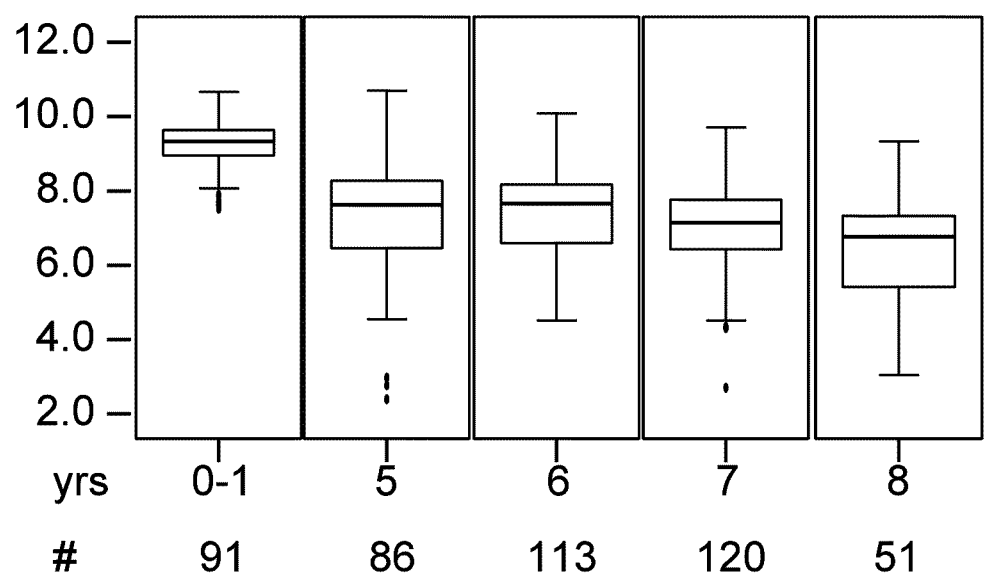

FIG. 5—qRT-PCR is efficient with demodified RNA isolated from paraffin-embedded tissue that was stored for 0 to 8 years in paraffin RNA that was isolated from tissue samples after storage at room temperature for the indicated period of time (yrs). The relative expression was determined from median Ct values for three stably expressed control genes (GUSB, beta glucuronidase, NM_000181.1; RPLP0, large ribosomal protein, NM_053275.3; UBB, ubiquitin B, NM_018955.2) from the indicated number of samples (#). Shown are relative expression values in arbitrary units (in log 2 scale). The expression decreases by approximately 0.3 units (in log 2 scale) per year of storage as paraffin-embedded tissue at ambient temperature.

Figure 6:
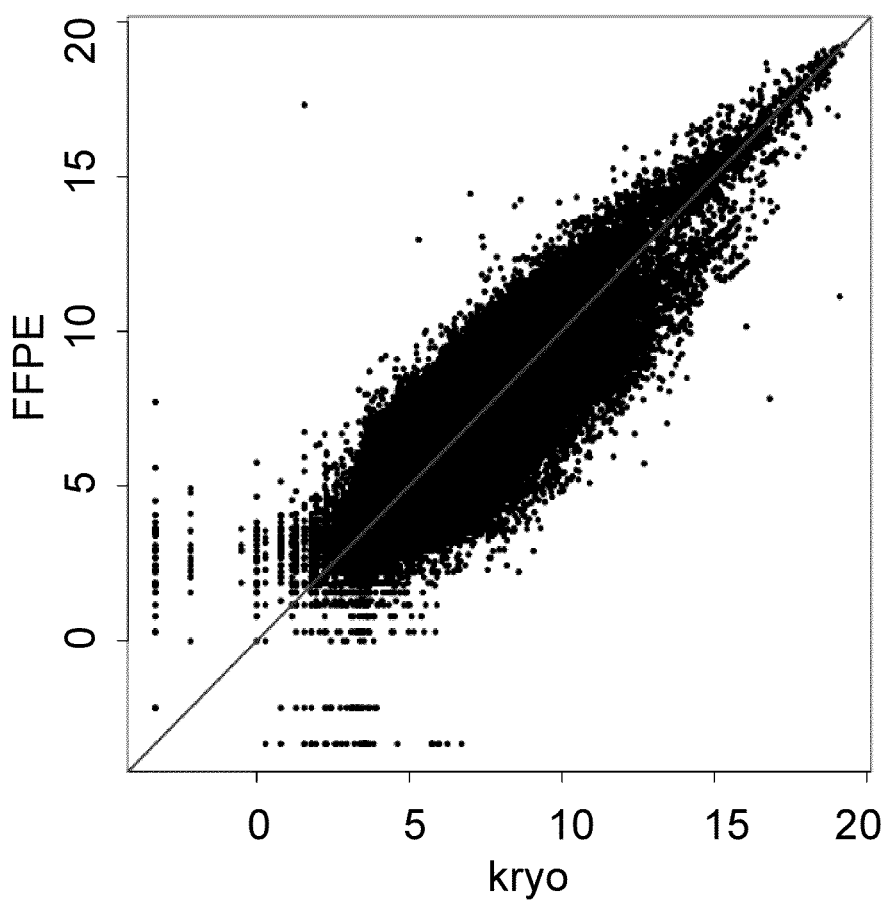

FIG. 6—Microarray analysis with RNA from fresh frozen and RNA derived of formalin-fixed and paraffin-embedded tissue of the same tumor RNA isolated from paired samples of fresh frozen (kryo) and FFPE material according to the method described in Example 2 are shown in a scatter plot. X-axis: RNA from fresh frozen material; Y-axis: FFPE-derived RNA.

DETAILED DESCRIPTION OF THE INVENTION

The present invention describes a novel method and a reagent for optimizing the recovery of RNA from tissue treated with formaldehyde, for example archival, formalin treated tissue that was stored for days, months or years in paraffin prior to RNA isolation. The method of the invention facilitates processing of archival samples for RNA extraction and down-stream applications involving reverse transcription, e.g. PCR, qRT-PCR and, especially, microarray analysis.

The method comprises treating an RNA containing sample with a solution containing an ammonium salt as a demodification medium that greatly reduces methylol groups in RNA and partly destroys methylene bridges between nucleotides within single RNA molecules, between two RNA molecules, and between RNA and protein at physical conditions which protect the RNA from additional degradation. In a preferred embodiment, the demodification medium is directly combined with RNA in a chaotropic extraction buffer. After demodification the RNA can be bound to silica-based columns and the demodification reagent is washed out together with cell debris.

The present invention is based on the observation that RNA from archival tissue is chemically modified and crosslinked with other molecules, and this prevents or inhibits many down-stream applications. Demodification improves the quality of RNA for many of these applications. The present invention describes methods for preparing nucleic acids and mainly RNA suitable for expression measurement particularly by qRT-PCR and microarray analysis. Archival tissue may be used from paraffin embedded blocks as thin sections, tissue punches usually prepared for tissue microarrays or from macro- or micro-dissected material. Demodification with an ammonium salt at elevated temperature according to the present invention greatly improves the procedure for RNA isolation from archival material. The demodification solution may have a particular concentration of components at the outset, and the concentration is decreased once the solution is added to the sample containing RNA. Accordingly, it has to be indicated whether the concentration of the components in the demodification solution is understood to refer to the concentration of the components prior to or after the addition to the sample.

To obtain optimal recovery of RNA from archival material it is necessary to homogenize the tissue and digest the cell lysate with a protease that is partially active in chaotropic reagents. Chaotropic reagents are needed to inactivate or inhibit intracellular RNases during this process. RNA isolation from samples which contain large amounts of RNases is challenging, and a procedure which inactivates RNases rapidly and efficiently may be required like, for example, homogenization in chaotropic agent (e.g. guanidinium thiocyanate) which solubilizes cell membranes and inactivates nucleases.

Archival tissue (FFPE material) is less convenient than fresh frozen or RNAlater® (Ambion) treated tissue, but nonetheless, it is of very high impact as many samples are exclusively available as pathological samples, and these are usually stored as FFPE blocks. For example, human biopsy samples are fixed in formalin and embedded in paraffin because the procedure maintains tissue architecture and epitopes for immunohistochemistry very well. Samples treated this way are stored in all pathologies worldwide and millions of samples exist.

Fixing and embedding tissue include the following main steps in which RNA degradation can occur:
1. After resection from the live organism isolated tissue samples usually are transported on ice or at room temperature to a pathological unit for further analysis. Many processes may be activated including exposure of cellular RNA to endogenous RNases, which are released from vesicles. This process cannot be influenced significantly, especially not for archival samples, which were taken at an earlier time point.
2. Fixation with formaldehyde is a slow process and penetration of formalin into the tissue occurs at a rate of about 1 mm per hour. Therefore, fixation takes several hours. Formalin is applied in aqueous solutions, wherein RNases may remain active at least for some time. Endogenous RNases will partially degrade RNA and this can probably not be prevented. This is opposite to specialized freezing or RNA preserving reagents which penetrate the tissue very rapidly and inactivate endogenous RNases before they degrade intracellular RNA. Later in the process the sample may be treated with alcohol, and RNases are no longer active or they are otherwise not available (e.g. precipitated from the solution). During paraffin embedding the tissue is heated to elevated temperatures; this may lead to a limited additional degradation.
3. Once the material is formalin-fixed and embedded in paraffin, blocks containing tissue may be stored for years at ambient temperature. At this stage the RNA is fairly stable.
4. RNA can be isolated from thin sections that are prepared on a conventional microtom. For this, sections are de-paraffinized and homogenized in aqueous buffer containing a chaotropic agent. Sections are homogenized with a polytrone, a tissue lyzer or an otherwise suitable method, which allows the chaotropic agent to penetrate the tissue and inactivate residual RNases, which may become re-activated once they get in contact with aqueous solution.
5. Alternatively, cylindrical punches of tissue can be taken from paraffin embedded tissue as they are used in tissue microarray (TMA). This tissue is also homogenized in chaotropic agent, and RNA is isolated from the homogenate.
6. Applications like tissue microdissection (LCM) require short staining reactions followed by a complete dehydration. Cells or small tissue areas of interest can then be isolated and transferred to individual small tubes, RNA can then be isolated separately from each tube as described for whole sections or tissue punches. During exposure of tissue sections to aqueous solutions RNases may be reactivated and therefore, molecules inhibiting RNases should be added during staining.

It is very important that tissue specimen used for RNA isolation are kept dry and in a water-free environment. In cases where aqueous solutions are required, e.g. during staining of sections, incubation periods should be kept short, the temperature should be low and inhibitors of RNase should be added to prevent further degradation of RNA.

If paraffin embedded tissue is used for RNA isolation, the paraffin has to be extracted in the first step. This is done by standard methods known in the art, for example extraction with xylene, ethylbenzene, toluene, chloroform, or a $C_9$-$C_{11}$ hydrocarbon mixture as is available from Merck (Merck KGaA, Darmstadt, Germany) under the trade name Neo-Clear™, optionally followed by a rehydration with aqueous alcoholic solutions of decreasing alcohol content. Alternatively deparaffinization and rehydration may be carried out simultaneously using e.g. a reagent such as EZ-DEWAX™ (BioGenex, San Ramon, Calif.).

Tissue samples free of paraffin are typically treated with a proteolytic enzyme such as proteinase K to degrade the structural components of the tissue, then the RNA is extracted with a solution containing 1 M to 5 M guanidinium salt. The RNA is purified from extraction and demodification solutions containing tissue debris and protease digested fragments e.g. on a silica-based column. The RNA recovered from fixed tissue contains partially fragmented RNA with fragment sizes of about 100 to greater than 500 bases. Fragmentation is probably due to a number of factors including the action of endogenous RNases, which remain active during (the initial phase of) fixation. Since all RNA molecules are mostly degraded into several pieces, such RNA cannot be used for Northern analysis or nuclease protection assays. However, the RNA can be used in normal RT-PCR and also in quantitative qRT-PCR, when amplifying amplicons which are usually less than 100 base pairs in length are used.

When attempting to isolate RNA from archival samples treated with formalin according to Danenberg et al. (US 2006/0199197) with a guanidinium-containing buffer and heating to 70-90° C., the recovery of RNA is not very consistent and the quality of the material does not meet the performance standards by the present invention. For most of the pathological samples of interest only limited material is available and a more efficient and robust method for RNA isolation is needed. The present invention provides such a method.

The use of an ammonium salt, e.g. ammonium chloride, according the invention greatly enhances reversion of chemical modifications in RNA or cross-links between RNA and protein or between RNA and other nucleic acids for formalin-fixed material.

The RNA demodification solution comprises an ammonium salt at a concentration from 0.1 M to 5 M or up to a saturating concentration. The ammonium salt is preferably ammonium chloride or ammonium formiate, but also any other ammonium salt may be used.

Specifically, salt concentrations of 6.3, 12.6, 18.9, 25.2, or 31.2 g ammonium chloride per 100 mL corresponding to 1 M, 2 M, 3 M, 4 M, and 5 M, respectively, may be used, and the concentration may be a range defined between any two of these concentrations. In a preferred commercial embodiment, the ammonium salt is ammonium chloride and it is added at a stock concentration of 31.2 g/100 mL (5 M). This stock solution may be provided in pre-measured aliquots, which are added to the sample containing RNA.

During use, some dilution of the salt concentration occurs due to, for example, liquid in the sample. Therefore, these specifically mentioned salt concentrations are higher than the final salt concentrations present in the sample during demodification. Further, it is contemplated that amounts of ammonium salt higher than the saturating concentration may be used in the present invention. In such embodiments, the salt may be added directly to the RNA containing medium. In fact, demodification mixtures having more than a saturating concentration of an ammonium salt have utility in applications where these mixtures are added to a liquid sample. In such cases, upon addition to the liquid sample, ammonium salt, which is not in solution prior to addition, will become soluble due to the increase in liquid volume. Thus, the final concentration of an ammonium salt can still be very high, in particular higher than if a 5 M stock solution is used.

The reaction is favored at elevated temperature and at pH values between 4.0 and 8.0. This pH is compatible with RNA and does not lead to hydrolysis.

The RNA demodification medium further comprises a chaotropic agent, in particular a guanidinium salt, such as guanidinium isothiocyanate, guanidinium thiocyanate or guanidinium chloride, in particular guanidinium isothiocyanate. This additional component protects the RNA by inhibiting RNases from degrading the RNA. Guanidinium containing buffers are usually used at 4 M concentration of guanidinium salt. As most RNases are irreversibly inactivated during formalin fixation the chaotropic reagent can be used at reduced concentrations, e.g. 1 M or 2 M without reducing the quality of the isolated RNA form archival material. It is preferred that the ammonium chloride is used together with the chaotropic reagent, but stepwise use is also possible.

The RNA demodification medium may comprise a proteinase such as proteinase K to destroy proteins and particularly RNases. Other proteinases are also contemplated, for example chymotrypsin, papain, pepsin, trypsin, pronase, and endoproteinase Lys-C. It is preferred that the ammonium chloride is used together with the optional proteinase, but stepwise use is also possible.

The RNA demodification medium may comprise other compounds, for example mild detergents, such as Triton X, Nonidet P40, Tween-20 or sodium deoxycholate, in particular Triton X-100, and buffers at pH between pH 4 and 8, preferably around pH 8, for example Tris-HCl, pH 8.0, to stabilize the pH of the tissue homogenate during solubilization and digestion with proteinase and during or before the addition of the ammonium salt to the lysate.

Typically, the RNA isolation medium comprises a buffer that maintains the lysate at a constant pH during denaturation and protease digestion. For example, the buffer can be Tris-HCl, or another buffering at pH 8.0. In the presently preferred commercial embodiment, the buffer is Tris-HCl pH 8.0.

The sample for RNA isolation may be any of a number of types of samples. For example, the sample may be a suspension of cells or tissue culture cells. Alternatively, the sample may be a solid tissue, for example a tissue sample from heart, liver, spleen, kidney, pancreas, or tissue biopsies from breast or prostate. The tissue may be normal tissue or diseased tissue, for example cancer tissue, infected material, or contaminated tissue. In many protocols, the tissue will be histological sections or tissue punches prepared from conventional paraffin embedded specimen.

The temperature during demodification may be any temperature between room temperature and 100° C., preferably between 50° C. and 94° C. The time for demodification is between 1 min and 24 hours, e.g. between 12 and 24 hours at room temperature, but preferably between 1 min and 3 h at elevated temperature, such as between 1 and 45 min at 94° C., between 20 and 60 min at 70° C., or between 0.5 and 3 hours at 50° C.

The components of the demodification solution can be added to the aqueous sample containing RNA in solid form to yield the desired final component concentration in solution. The solid components can be provided as powders, tablets, pills or other suitable formulations that provide the desired properties of demodification medium. Solid components in pre-measured aliquots can be directly added to a sample, added to a sample/liquid mixture, or may be present in a collection vessel prior to collection of a sample or sample/liquid mixture. In a typical protocol, the solid components of the present invention are added after proteinase digestion of the sample containing RNA and prior to sample purification on silica columns.

Tablets are a convenient form for storage of the solid components of the demodification solution, and they can be added in the correct quantity to the sample of any size in any type of vial. The RNA demodification reagent containing predetermined final salt concentrations or supersaturated salts can be supplied as packages. The RNA preservation salt or supersaturated salt packages are especially useful in routine settings, as they can be added in a setting with limited space or absence of analytical equipment (micropipettes). For example, the demodification reagent components can be supplied as pre-measured and packaged tablets or liquid aliquots for defined volumes of RNA lysis reagent usually used during standard isolations preceding demodification, e.g. 0.5 mL, 1 mL, 5 mL RNA sample size. Of course, any packet size could be provided to accommodate a variety of experimental conditions as a powder, or a liquid packaged at preferred volumes, or as a solid in form of tablets. Thus, one simply adds the package content to the protease digested RNA sample, mixes, heats to the desired temperature, and thereby starts demodification.

Certain advantages of using a solid component RNA demodification reagent are weight savings in storage and transport, avoidance of spills, and minimizing volumes. Dry powder, pellets and tablets also minimize the risk of bacterial growth during storage.

Particularly preferred conditions are 5 M ammonium chloride at pH 5.2 for demodifying RNA isolated from archival tissue samples at temperatures ranging from 70-94° C.

The demodification reagent used according to the present invention functions by reducing the chemical binding of methylol bound to amino groups in nucleobases causing the regeneration of an amino group in nucleobases. Importantly, the RNA backbone is not affected and remains intact. Upon application to the sample, the ammonium chloride favors the reversion of chemical bonds between methylol and amino groups in nucleobases of RNA (or also of DNA) and in amino groups of amino acid residues (e.g. lysine) and proteins. To some extent methylene bridges between RNAs, and between RNA and protein are also cleaved during demodification. The result of cleavage of a methylene bridge between RNAs is a fully restored nucleobase with an amino group and a nucleobase with a remaining methylol group attached to the amino group in a 1:1 ratio. Cleavage of methylene bridges between RNA and protein will lead to a restored nucleobase and a methylol group attached to the amino group of the amino acid residue. The methylol group may then be cleaved from the amino group of RNA or protein in a second step.

The RNA can be used for gene expression measurement by polymerase chain reaction (PCR) and variations thereof, such as quantitative PCR (qPCR), reverse transcription PCR (RT-PCR), and real-time PCR. Such methods utilize one or two primers that are complementary to portions of a disclosed sequence, wherein the primers are used to prime nucleic acid synthesis. The newly synthesized nucleic acids are optionally labelled and may be detected directly. Suitable labels are radioisotopes, nucleotide chromophores, enzymes, enzyme substrates, fluorescent molecules, chemiluminescent moieties, magnetic particles, bioluminescent moieties, and the like.

The RNA can also be used for microarray analysis. A microarray is a linear, a two-dimensional or a three dimensional array of preferably discrete regions, each having a defined area, formed on the surface of a solid support, such as glass, plastic, or synthetic membrane or a porous layer. The density of the discrete regions on a microarray is determined by the total numbers of immobilized polynucleotides to be detected on the surface of a single solid phase support, preferably at least 1,000/cm. The arrays may contain any number of immobilized polynucleotides, e.g. between 500 and more than several hundred thousand immobilized polynucleotides in total. A DNA microarray is an array of oligonucleotides or polynucleotides placed on a chip or other surfaces used to hybridize to amplified or cloned polynucleotides from a sample. Since the position of each particular group of probes in the array is known, the identities of sample polynucleotides can be determined based on their binding to a particular position in the microarray. The polynucleotides may contain minor mismatches which do not affect hybridization to the nucleic acids of a sample.

Preferably, the present invention is used to identify mRNA sequences that are over- or under-expressed in tissue pretreated with formaldehyde, e.g. in formalin fixed, paraffin embedded tissue. One embodiment of the invention involves determining expression by hybridization of mRNA isolated from such tissue, or an amplified or cloned version thereof.

In particular, this goal is accomplished by isolating RNA from tissue, optionally purifying it over a silica based column, synthesizing cDNA in the presence of a T7 RNA polymerase primer carrying 7 to 20 fully randomized deoxynucleotides oligo (dN) at the 3' end, for example a $(dN)_{10}$-T7 primer 5'-GAATGGTAATACGACTCACTATAGG-GAGANNNNNNNNNN-3' (SEQ ID NO:1), transcribing the obtained cDNA in the presence of T7 RNA polymerase and labelled nucleotides, hybridizing the obtained RNA with a DNA microarray chip, and determining RNA by measuring labelled positions on the microarray.

dN stands for any deoxynucleotide, i.e. adenosine, guanosine, thyimidine or cytidine. Random oligonucleotides are synthesized by providing simultaneously all nucleotides during synthesis. This leads to an equal distribution of all nucleotides at the respective positions in the primer DNA. Upon mixing such primers with mRNA isolated from tissue they can hybridize to RNA in regions of homology, and all regions of the RNA have a similar chance to bind such an oligonucleotide. When a cDNA is synthesized from these primers by adding an appropriate RNA-dependent DNA polymerase, the resulting cDNA represents the entire mRNA sequence and no 3' end bias is observed as is observed typically when standard oligo(dT)-T7 primers are used. Using a bacteriophage T7 RNA polymerase primer carrying 7 to 20 fully randomized deoxynucleotides at the 3' end for RNA amplification is a further particular aspect of the present invention.

The obtained cDNA is converted to a double stranded DNA by the addition of a DNA polymerase. The synthetic T7 promoter introduced during cDNA synthesis is used for in vitro transcription in the presence of bacterial T7 polymerase. During this process the RNA is amplified and labelled, when transcription is performed in the presence of nucleotides carrying a fluorescent label such as Cy3. This may be accomplished, for example, following the detailed protocol for "Low RNA Input Fluorescent Linear Amplification Kit" available from Agilent (Agilent Technologies, Inc., Santa Clara, Calif.). Amplified RNA is optionally purified on silica-based columns, and labelled RNA is hybridized to microarray chips carrying DNA. After hybridization, chips are washed according to the protocols of the manufacturer, and chips are scanned to detect immobilized labels according to standard protocols. Signals measured from each area of the chip represent expression values for individual genes.

Having now generally described the invention, the same will be more readily understood through reference to the following examples which are provided by way of illustration, and are not intended to be limiting of the present invention.

EXAMPLES

Example 1

Heat Treatment of Lysate in the Presence of Demodification Solution

A breast cancer specimen is fixed in 4% buffered formalin and embedded in paraffin. 10 µm thick sections are homogenized in lysis buffer (4 M guanidine isothiocyanate, 30 mM Tris pH 8.0, 1% Triton-X-100), and digested with 1 mg/mL proteinase K for 1 h at 55° C. The reaction volume is diluted with 5 volumes of 30 mM Tris pH 8.0, 1% Triton X-100, and another aliquot of proteinase K (1 mg/mL final concentration) is added and digestion continued for 1 h at 55° C. Then, 25% (vol./vol.) of demodification solution (5 M ammonium chloride) is added and the lysate incubated at 94° C. for 0, 30, 60, 120 or 300 min. After addition of ethanol (final concentration 55% (vol./vol.)) the lysate containing the RNA is purified on a silica-based column (EconoSpin Mini Spin Columns, Epoch Biolabs, Inc., Huston, Tex. USA).

Figure 1:
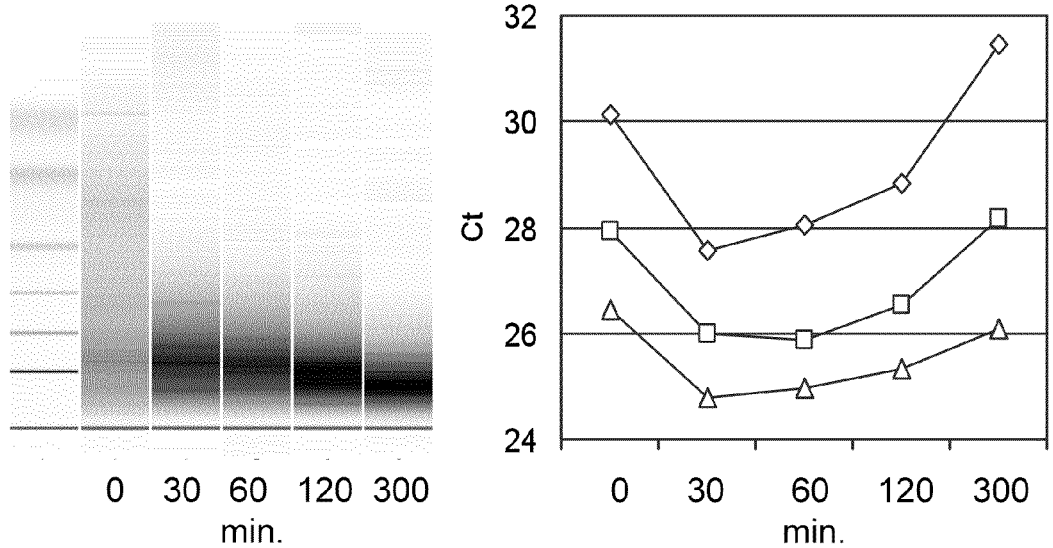
FIG. 1—Heat treatment of lysate in the presence of demodification solution

The purified RNA is analyzed on an RNA 6000 Nano chip and an Agilent 2100 Bioanalyzer. Each RNA is tested by qRT-PCR for the expression of GAPDH (glyceraldehyde-3-phosphate dehydrogenase, accession number: NM_002046.3) using forward and reverse primers coding for short (forward: 5'-CAGCCGCATCTTCTTTTGC-3', SEQ ID NO:2; reverse: 5'-CCATGGTGTCTGAGCGATGT-3', SEQ ID NO:3; probe: 5'-TCGCCAGCCGAGC-3', SEQ ID NO:4; amplicon size 54 bp), medium-length (reverse: 5'-ACCAGGCGCCCAATACG-3', SEQ ID NO:5; amplicon size 83 bp) and long amplicons (reverse: 5'-GCAACAATATCCACTTTACCAGAGTTAA-3', SEQ ID NO:6; amplicon size 103 bp). The resulting threshold cycle values are shown in FIG. 1 for each amplicon.

Example 2

Microarray Analysis with RNA from Fresh Frozen and RNA Derived of Formalin-fixed and Paraffin-Embedded Tissue of the Same Tumor The RNA from human breast cancer is isolated from paired samples of fresh frozen and FFPE material. The RNA is isolated from four 25 μm thick cryo sections according to standard procedures. For FFPE material, three to ten 10 μm thick paraffin sections (depending on the size of the tissue) are deparaffinized with Neo-Clear™ (Merck KGaA, Darmstadt, Germany) and homogenized with a tissue lyzer (Mixer Mill, Retsch GmbH, Haan, Germany), a polytrone or another suitable instrument to disrupt the tissue in 200 μL of lysis buffer containing 0.67 M guanidine isothiocyanate, 30 mM Tris pH 8.0, 1% Triton X-100. The proteinase K (1 mg/mL) is added before or after homogenization and the lysate is digested for 1 hour at 55° C. The RNA in the lysate is demodified by adding ammonium chloride to a final concentration of 2.5 M and incubating at 94° C. for 30 min. The RNA is purified from the lysate on silica-based columns (EconoSpin Mini Spin Columns, Epoch Biolabs, Inc., Huston, Tex. USA). cDNA is synthesized in the presence of random $N_{10}$-T7 primer 5'-GAATGGTAATACGACTCACTATAGG-GAGANNNNNNNNNN-3' (SEQ ID NO:1). Single stranded cDNA is converted to double stranded cDNA according to standard procedures. The cDNA is used as template for T7-mediated in vitro RNA synthesis in the presence of Cy3-labelled nucleotides according to standard procedures for the synthesis of probes for DNA chip experiments. The resulting amplified RNA is fragmented to smaller fragments and hybridized to 44 k Agilent chips. Chips are washed and scanned according to the protocol for "Low RNA Input Fluorescent Linear Amplification Kit", available from Agilent (Agilent Technologies, Inc., Santa Clara, Calif.). A scatter plot depicting data from cryo- and FFPE-derived RNAs of the same tumor specimen is shown in FIG. 6. Each spot on the chip represents the signal intensity of one oligonucleotide representing a single human gene. Signal intensities measured from probes derived of fresh frozen material are plotted on the X-axis, probes derived of FFPE material are plotted on the Y-axis. The same experiment with pairs of cryo- and FFPE-derived RNA samples was performed from six independent tumors and the mean of % "present calls" on the chip and the Pearson correlation between signals from fresh frozen and FFPE are summarized in the Table. "Present calls" are spots which revealed signals above background after hybridization. Pearson correlation (Pearson corr.) is used to describe the similarity between signals from fresh frozen and FFPE RNAs.

While the present invention has been illustrated and described with respect to a particular embodiment thereof, it should be appreciated by those of ordinary skill in the art that various modifications to this invention may be made without departing from the spirit and scope of the present.

TABLE

| | # of features | % present | samples | Pearson corr. |
|---|---|---|---|---|
| intact (cryo) RNA | 39900 | 88% | 6 | 0.78 |
| FFPE RNA | 33600 | 74% | 6 | |
| Total number of features | 45220 | | | |

The invention claimed is:

1. Method for the isolation of RNA from tissue pretreated with formaldehyde comprising the steps of (a) homogenizing the tissue sample in the presence of a guanidinium salt in aqueous solution, and (b) incubating the sample in the presence of 0.1 M to 5 M ammonium salt at a temperature between 50° C. and 100° C.

2. The method of claim 1, wherein the tissue pretreated with formaldehyde is formalin fixed, paraffin embedded tissue.

3. The method of claim 1, wherein the aqueous solution of step (a) further comprises a detergent.

4. The method of claim 1, wherein the aqueous solution of step (a) further comprises a buffer pH 4 to 8.

5. The method of claim 1, wherein proteinase K is added to the solution of step (a).

6. The method of claim 1, wherein the ammonium salt of step (b) is ammonium chloride.

7. The method of claim 1, wherein the ammonium salt of step (b) is added to the solution of step (a) as an approx. 5 M stock solution or in solid form.

8. The method of claim 1, wherein incubation in step (b) is between 1 and 300 minutes.

9. The method of claim 8, wherein incubation in step (b) is between 1 and 45 min at around 94° C.

10. The method of claim 8, wherein incubation in step (b) is between 20 and 60 min at around 70° C.

11. The method of claim 8, wherein incubation in step (b) is between 0.5 and 3 hours at around 50° C.

12. The method of claim 1, further comprising the step of separating RNA from cell debris and reagents on a silica gel column.

13. The method of claim 1, further comprising the step of determining RNA with reverse transcriptase-polymerase chain reaction, wherein one or two primers that are complementary to portions of a disclosed sequence are used to detect whether such a disclosed sequence is present in the isolated RNA.

14. The method of claim 1, further comprising the step of determining RNA with DNA microarray technology, wherein isolated RNA is amplified or cloned, added to an array of immobilized polynucleotides, hybridization to immobilized polynucleotides is measured, and the presence and / or identity of the original isolated RNA determined based on its binding to a particular position in the microarray.

15. The method of claim 14, comprising the steps of synthesizing cDNA in the presence of a T7 RNA polymerase primer carrying 7 to 20 fully randomized deoxynucleotides at the 3' end, transcribing the obtained cDNA in the presence of T7 RNA polymerase and labelled nucleotides, hybridizing the obtained RNA with a DNA microarray chip, and determining the presence and/or identity of RNA by measuring labelled positions on the microarray.

* * * * *